(12) United States Patent
Rastrelli et al.

(10) Patent No.: US 11,278,484 B2
(45) Date of Patent: Mar. 22, 2022

(54) SKIN CARE COMPOSITIONS COMPRISING A NON-HYDROLYZED NUCLEIC ACID MATERIAL EXTRACTED FROM TUNA

(71) Applicant: KALICHEM SRL, Rezzato (IT)

(72) Inventors: Gianbattista Rastrelli, Rezzato (IT); Francesco Rastrelli, Rezzato (IT)

(73) Assignee: Kalichem SRL, Rezzato (IT)

( * ) Notice: Subject to any disclaimer, the term of this patent is extended or adjusted under 35 U.S.C. 154(b) by 0 days.

(21) Appl. No.: 17/435,528

(22) PCT Filed: Mar. 4, 2020

(86) PCT No.: PCT/EP2020/055619
§ 371 (c)(1),
(2) Date: Sep. 1, 2021

(87) PCT Pub. No.: WO2020/178306
PCT Pub. Date: Sep. 10, 2020

(65) Prior Publication Data
US 2022/0040078 A1    Feb. 10, 2022

(30) Foreign Application Priority Data

Mar. 5, 2019  (IT) .................. 102019000003165

(51) Int. Cl.
| | | |
|---|---|---|
| *A61K 35/60* | (2006.01) | |
| *A61K 8/60* | (2006.01) | |
| *A61Q 19/08* | (2006.01) | |
| *A61K 8/98* | (2006.01) | |

(52) U.S. Cl.
CPC .............. *A61K 8/606* (2013.01); *A61Q 19/08* (2013.01); *A61K 8/987* (2013.01)

(58) Field of Classification Search
CPC .................................................. A61Q 19/08
See application file for complete search history.

(56) References Cited

U.S. PATENT DOCUMENTS

| | | |
|---|---|---|
| 5,194,253 A | 3/1993 | Garrido |
| 5,547,684 A | 8/1996 | Vainberg et al. |
| 2002/0064508 A1 | 5/2002 | Lyles |

FOREIGN PATENT DOCUMENTS

| | | | |
|---|---|---|---|
| JP | 59134706 A | | 8/1984 |
| JP | 2015523333 A | | 8/2015 |
| KR | 20070061985 A | | 6/2007 |
| KR | 20100127086 A | * | 12/2010 |
| KR | 20100127086 A | | 12/2010 |
| WO | 2012101473 A1 | | 8/2012 |
| WO | 2020178306 A1 | | 9/2020 |

OTHER PUBLICATIONS

Written Opinion of the international Search Authority for PCT/EP2020/055619 dated May 18, 2020.
International Search Report for PCT/EP2020/055619 dated May 18, 2020.

\* cited by examiner

*Primary Examiner* — Qiuwen Mi
(74) *Attorney, Agent, or Firm* — Vorys, Sater, Seymour and Pease LLP; Iona Niven Kaiser

(57) ABSTRACT

The present invention relates to a non-therapeutic cosmetic method—for enhancing the overall quality of the skin and for treating aging skin which comprises the use of non-hydrolyzed nucleic acid material extracted from tuna containing more than 75% by weight of DNA salts and less than 1.5 wt % of proteins, and to a non-therapeutic cosmetic composition for topical application onto the skin comprising from 0.01 to 5.0% by weight of said non-hydrolyzed nucleic acid material in a cosmetic or pharmaceutical acceptable carrier.

8 Claims, No Drawings

SKIN CARE COMPOSITIONS COMPRISING A NON-HYDROLYZED NUCLEIC ACID MATERIAL EXTRACTED FROM TUNA

TECHNICAL FIELD

The present invention relates to a non-therapeutic cosmetic method for enhancing the overall quality of the skin and for treating aging skin, which comprises the use of non-hydrolyzed nucleic acid material extracted from tuna containing more than 75% by weight of DNA salts and less than 1.5 wt % of proteins.

The present invention also relates to a non-therapeutic cosmetic composition for topical application onto the skin comprising from 0.01 to 5.0% by weight of said non-hydrolyzed nucleic acid material and a cosmetic or pharmaceutical acceptable carrier.

PRIOR ART

In all living bodies, including human beings, organs, such as the skin, gradually deteriorate, as they grow old. As the skin ages, protection of the skin against stimulation, such as oxidation stress, weakens to cause the conditions inside the skin to be bad, thus promoting the aging. Several factors contribute to the aging of skin, leading to accelerated deterioration evidenced by wrinkles and sagging of the skin; for example the excessive exposure to ultraviolet radiation and sunlight causes skin to look prematurely aged. Because of skin aging, deep changes happen at both dermis and epidermis levels. In particular, the skin loses its elasticity: the skin does not snap back when pinched and wrinkles, stretch marks and sagging are more obvious as result of free radicals on the body.

A major concern in the improvement of skin-care has been treating the signs of aging, especially on the face and on the part of the body more subjected to stress. As such, there are many bioactive compounds on the market directed towards fighting various skin conditions associated with loss of skin elasticity and firmness, such as folds in the eyelids, skin sagging, and other aging signs such as fine lines, wrinkles and so on.

Many of these bioactive compounds are isolated from by-products generated by meat and seafood processing industries. For example, nucleic acid materials, such as DNA, extracted from young bovines or fishes, have been proposed in many patent applications and scientific articles for care treatment of mature skin. These nucleic acid materials are typically used as skin protectants and moisturizing agents.

JP 59-134706 discloses cosmetics containing substances relating to nucleic acid such as DNA, humectants and further desirably physiologically active ingredients, which show excellent effects in skin protection and moisture retention.

U.S. Pat. No. 5,194,253 describes an aqueous gel containing alkaline salt or ammonium salt of hyaluronic acid, mineral or organic salt of high molecular weight DNA, and a hydrophilic polymer. The gel is proposed as a facial mask.

U.S. Pat. No. 5,547,684 describes cosmetic preparations containing DNA-sodium salt useful for the treatment of aging skin and skin problems. The DNA is extracted from various fish reproductive cells using a sodium chloride solution. US 2002/064508 relates to sunscreen formulations containing nucleic acids obtained from calf thymus and fish (e.g. salmon or herring) sperm.

KR 2007/0061985 relates to health-food compositions having an antioxidant and immune-enhancing function containing nucleic acid material extracted from tuna testis together with vitamins, collagen, selenium, and magnesium stearate. The nucleic acid material contains nucleic acids and proteins in a ratio 2:1.

KR 2010/0127086 discloses cosmetic compositions containing hydrolyzed nucleic acid complexes isolated from tuna testis, having anti-oxidation, UV absorption, anti-aging and anti-wrinkling properties.

WO 2012/101473 is aimed to the development of an effective method of skin treatment with formulations based on aqueous dispersions of metal oxides, DNA of natural origin and other additional ingredients.

However, since skin-care needs vary from person to person, no single products suits every individual. Thus, there is always a need for new and improved products, which are effective in the treatment of skin conditions associated with aging and with a good compatibility for sensitive skin types. Moreover, since there is a number of people showing allergic reactions to proteins, they should be absent as much as possible from these products.

The inventors of the present invention have now discovered, surprisingly and unexpectedly, that a non-hydrolyzed nucleic acid material extracted from tuna, with a high content of DNA salts and a low content of proteins, gives cosmetic advantages when used as an anti-aging ingredient for topical applications on skin.

In fact, the non-hydrolyzed nucleic acid material with a high content of DNA salts and a low content of proteins is highly compatible with the cosmetic raw materials and allows preparing homogeneous cosmetic compositions for topical application having a more pleasant appearance, a higher stability and less prone to induce allergic reactions.

As far as the Applicant knows, none has described the application on the human skin of a nucleic acid material extracted from tuna with a high content of non-hydrolyzed DNA salts and a low content of proteins.

KR 2010/0127086 describes nucleic acid complexes obtained from tuna testis, but it is clearly specified that the expression "nucleic acid complex" means a mixture comprising nucleic acids and other substances, somehow bound/interacting with the nucleic acids. These further substances, mainly carbohydrates, lipids, proteins and ashes, are present in large quantities, as shown in Table 2 of the application.

In addition, the nucleic acid complexes of KR 2010/0127086 were subjected to a specific hydrolytic treatment to reduce their molecular weight.

On the contrary, the DNA salts of the present invention are not bound/interacting with other substances, such as protein and carbohydrates, and it can be supposed that they are more available for being completely absorbed and incorporated in cells of the skin and the connective tissue. For this reason, they can be used more effectively for the synthesis of new DNA in the cells of the skin, increasing its regenerative power.

Moreover, not being subjected to a hard chemical treatment, the non-hydrolyzed nucleic acid materials of the present invention retain all their biological compatibility and activity.

With the expression "DNA salt", we mean a inorganic or organic salt of DNA, such as alkali, alkaline earth, transition metal, ammonium and amino acid salts of DNA.

DESCRIPTION OF THE INVENTION

It is therefore an object of the present invention a non-therapeutic cosmetic method, which comprises the topical application onto the skin of a non-hydrolyzed nucleic acid material extracted from tuna containing more than 75% by weight (wt %), preferably more than 80 wt %, of DNA salts and less than 1.5 wt % of proteins.

It is another object of the invention a non-therapeutic cosmetic composition for topical application onto the skin comprising from 0.01 to 5.0 wt %, preferably from 0.03 to 3 wt %, of said non-hydrolyzed nucleic acid material extracted together with one or more acceptable cosmetic or pharmaceutical carriers or diluents.

It is a further object of the invention a non-hydrolyzed nucleic acid material extracted from tuna containing more than 75% by weight, preferably more than 80 wt %, of DNA salts and less than less than 1.5 wt %, preferably less than 1 wt %, of proteins.

DETAILED DESCRIPTION OF THE INVENTION

The DNA salts of the invention can be prepared, for example, by a process comprising the following steps:
I. homogenizing the tuna gonads or sperm in an aqueous solution of sodium chloride and sodium citrate to obtain a homogenized material;
II. sequentially adding to said homogenized material:
   a) an aqueous solution of sodium chloride and sodium citrate,
   b) an aqueous solution of an anionic surfactant, and
   c) a concentrated aqueous sodium chloride solution; and then carefully mixing the mass;
III. separating the solid fraction (proteins and lipid material) and recovering the liquid fraction;
IV. precipitating the nucleic acid material from the liquid fraction using an organic solvent;
V. recovering the nucleic acid material containing more than 75 wt % of DNA-sodium salt.

Usually, the aqueous solution for the homogenization of the biological material contains from 0.01 to 0.8 M, preferably from about 0.02 to 0.2 M, of sodium chloride and from 0.001 to 0.05 M of sodium citrate. The ratio between the tuna gonads or sperm and the aqueous solution I. is in the range comprised between 1:1 and 1:2 wt/vol. Typically, the homogenization is carried out in a blender for from 30 seconds to 15 minutes at a temperature comprised between 10 and 40° C.

In the second step, the homogenized material is placed in a reaction vessel equipped with a heating/cooling jacket and a mechanical stirrer, and the following aqueous solutions are added sequentially under stirring:
a) from 0.01 M to 0.8 M of sodium chloride and from 0.001 to 0.03 M of sodium citrate solution;
b) from 0.1 to 6% by weight of an anionic surfactant solution, and
c) from 1 M to 4 M of a sodium chloride solution.

The second step allows breaking the cell walls and membranes, to denature the proteins, to separate the proteins from nucleic acid and subsequently to remove the proteins in the form of sediment.

The temperature in the reaction vessel is usually maintained within the range of from 20 to 80° C. for a period ranging from 2 to 24 hours.

Examples of suitable anionic surfactants include sodium dodecyl sulfate, sodium xylene sulfonate, sodium benzoate and the like.

The liquid fraction containing the nucleic acids is separated from the reaction mass in the third step, preferably by centrifugation and/or by filtration. A filter aid, such as diatomaceous earths, can be added to the reaction mass to prevent blockage of the filter.

In the last step, the nucleic acid material is separated from the liquid fraction by precipitation with an organic solvent, such ethanol or isopropanol, usually in a 1:1 to 1:2 by volume liquid fraction/solvent ratio. Optionally, a small amount of an aqueous solution of an alkali salt can be added to the organic solvent to improve the precipitation efficiency.

The nucleic acid material is usually recovered by centrifugation. The pellet obtained from centrifugation can be subjected to further washing steps with the organic solvent to increase the purity of the product.

Preferably, the precipitation and subsequent washings are performed at a temperature below 15° C.

Finally, the non-hydrolyzed nucleic acid material can be dried at a temperature below 80° C. and milled to obtain a fine white powder.

Sodium chloride can be substituted by salts of other strong acids such sodium sulfate and sodium phosphate, and the like.

Sodium salts of other weak acids can be used instead of sodium citrate, for example, sodium acetate, ethylenediaminetetraacetic acid disodium salt and the like.

The sodium salts of this process can be substituted by other alkali, alkaline earth, transition metal salts, or ammonium and amino acid salts, such as potassium chloride and potassium citrate, magnesium chloride and magnesium citrate, zinc chloride, zinc citrate, ammonium chloride and ammonium citrate, lysine chloride and arginine chloride.

This process of extraction from the tuna gonads or sperm allows obtaining non-hydrolyzed nucleic acid material containing different DNA-salts, such as DNA-sodium salt, DNA-potassium salt, DNA-magnesium salt, DNA-zinc salt, DNA-ammonium salt, DNA-Arginine salt, DNA-Lysine salt, DNA-Hystamine salt and the like. The preferred DNA salt is DNA-sodium salt.

It is a fundamental characteristic of the nucleic acid material of the invention the fact that it has not been subjected to any hydrolytic process which can reduce its average molecular weight and modify its cosmetic performances. The nucleic acid material so obtained contains more than 75% wt %, preferably more than 80 wt %, more preferably more than 85 wt %, of DNA salts and less than 1.5 wt % of proteins. Preferably, it contains less than 1 wt % of proteins, more preferably less than 0.8 wt %.

The difference to 100% of the material is made up of carbohydrates, lipids, process by-products such as inorganic/organic salts, and, in particular, volatile substances, for example moisture and organic solvents. Preferably, the nucleic acid material contains less than about 20 wt % of volatile matter. The kinematic viscosity of a 0.06% by weight water solution of the non-hydrolyzed nucleic acid material of the invention, measured with a Ostwald viscosimeter, ranges from 10 to 150 mm$^2$/s, corresponding to a molecular dimension of the genomic fragments of about 50-250 kDa.

The non-hydrolyzed nucleic acid material of the present invention can be formulated into non-therapeutic cosmetic compositions for topical application onto the skin together with one or more suitable cosmetic or pharmaceutically acceptable carriers or diluents.

Suitable cosmetic or pharmaceutical acceptable carrier and diluents are well known in the art and can be of a variety of forms. They can be solvents or dispersion mediums containing, for example, water, ethanol, polyols (for example glycerol, propylene glycol, liquid polyethylene glycol and the like), oils and suitable mixtures thereof. The typical carrier/diluent can be in the form of an aqueous or hydro-alcoholic system, of an emulsion or of a gel; emulsions also include microemulsion systems.

Preferably, the composition for topical application is provided in emulsion form, this emulsion requires the presence of an emulsifier and oils (water insoluble) which are well known in the art.

The non-therapeutic cosmetic composition for topical application in emulsion form of the invention can comprise from 0.1 to 15.0% by weight of an emulsifier and from 1.0 to 60% by weight of an oil.

Oils include hydrocarbon oils and waxes, silicone oils, fatty acid derivatives, cholesterol, cholesterol derivatives, diglycerides, triglycerides, natural oils, natural oil derivatives, alkyl or alkenyl esters, lanolin and its derivatives, wax esters, beeswax derivatives and sterols and combinations thereof.

Examples of hydrocarbon oils and waxes suitable for use herein include petrolatum, mineral oil, micro-crystalline waxes, polyalkenes, paraffins, cerasin, polyethylene, perhydrosqualene, poly alpha-olefins, hydrogenated polyisobutenes and combinations thereof.

Examples of silicone oils suitable for use herein include dimethicone copolyol, dimethylpolysiloxane, diethylpolysiloxane, mixed $C_1$-$C_{30}$ alkyl polysiloxanes, phenyl dimethicone, dimethiconol and combinations thereof.

Examples of natural oils and derivative thereof suitable for use herein include castor oil, soy bean oil, derivatized soybean oils such as maleated soy bean oil, safflower oil, cottonseed oil and derivatized cottonseed oil, corn oil, walnut oil, peanut oil, olive oil, cod liver oil, almond oil, palm oil and sesame oil, sunflower seed oil, coconut oil and derivatized coconut oil, cocoa butter, and combinations thereof.

Examples of alkyl esters suitable for use herein include cetyl ricinoleate, stearyl ricinoleate, hexyl laurate, isohexyl laurate, myristyl myristate, decyl oleate, isodecyl oleate, hexadecyl stearate, decyl stearate, isopropyl isostearate, dihexyldecyl adipate, diisopropyl sebacate, lauryl lactate, myristyl lactate, cetyl lactate, and combinations thereof.

Examples of alkenyl esters suitable for use herein include oleyl myristate, oleyl stearate, oleyl oleate, and combinations thereof.

Examples of lanolin and lanolin derivatives suitable for use herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol ricinoleate, hydroxylated lanolin, hydrogenated lanolin and combinations thereof.

Other suitable oils include milk triglycerides (e.g., hydroxylated milk glycerides) and polyol fatty acid polyesters.

Still other suitable oils include wax esters, vegetable waxes and sterols, non-limiting examples including beeswax and beeswax derivatives, stearyl stearate; carnauba and candelilla waxes; cholesterol, ceramides; and combinations thereof.

Suitable emulsifiers are well known in the art and include nonionic, anionic, amphoteric, zwitterionic, cationic emulsifier and mixtures thereof. Examples of emulsifiers include also natural or synthetic polymeric emulsifiers.

Anionic emulsifier include alkyl and alkyl ether sulfates, alkyl sulfonates, alkyl and alkyl ether phosphates, alkyl or alkyl ether sulfosuccinates, alkyl and alkyl ether carboxylates and anionic derivatives of alkyl polyglycosides, such as the citric, tartaric or sulfosuccinic ester of alkyl polyglucosides.

Nonionic emulsifiers can be broadly defined as compounds containing a hydrophobic moiety and a nonionic hydrophilic moiety. Examples of the hydrophobic moiety can be alkyl, alkyl aromatic, and aryl aromatic. Examples of hydrophilic moieties are polyoxyalkylenes, amine oxides, and alkanol amides. Examples of non-ionic emulsifiers are alkoxylated fatty alcohols or fatty acids, alkoxylated di- and tri-stiryl phenols, polyhydroxy fatty acid amides, sugar esters and polyesters, alkoxylated sugar esters, sorbitan and alkoxylated sorbitan fatty acid esters. Other examples of nonionic emulsifiers include alkyl polyglycosides, such as coco polyglucosides.

Cationic emulsifiers useful in the non-therapeutic cosmetic composition for topical application of the present invention contain amino or quaternary ammonium hydrophilic moieties which are positively charged when dissolved in water. Examples of ammonium compounds are long-chain alkyl trimethyl ammonium chloride, long-chain alkyl benzyl dimethyl ammonium chloride, alkylamine hydrochlorides, alkylamine acetates and di(long-chain alkyl) dimethyl ammonium bromide.

The amphoteric emulsifiers which can be used in the composition for topical application of the present invention are those which can be broadly described as derivatives of aliphatic quaternary ammonium compounds, wherein one of the aliphatic substituents contains an anionic water-solubilizing group, e.g., carboxylate, sulfonate, sulfate. Examples of amphoteric surfactants include cocoamphocarboxypropionate, cocoamphoacetate, cocoamphodiacetate, sodium lauroamphoacetate.

Examples of zwitterionic surfactants include alkyl betaines and amido betaines, alkyl sultaines, alkyl glycinates and alkyl carboxyglycinates. Polymeric emulsifiers that are suitable for use herein include, but are not limited to, carboxylic acid polymers which are compounds, optionally crosslinked, containing one or more monomers derived from acrylic acid, substituted acrylic acids, and salts and derivatives of these acrylic acids and substituted acrylic acids. These carboxylic acid polymers also act as thickening agents.

They can be crosslinked homopolymers of a acrylic acid or of a derivative thereof, such as acrylamidopropylsulfonic acid. They can be also crosslinked copolymers having (i) a first monomer selected from the group consisting of (meth) acrylic acid, derivatives thereof, short chain (i.e. $C_1$-$C_4$) acrylate ester monomers, and mixtures thereof; and (ii) a second monomer which is a long chain (i.e. $C_8$-$C_{40}$) substituted polyethylene glycol acrylate ester monomer. Examples of commercially available carboxylic acid polymers useful herein are Carbopol 1342, Pemulen TR-1, Pemulen TR-2 (from Lubrizol Corp.); Sepigel 305, Simulgel EG, Simulgel NS, Simulgel 600 (from Seppic S.A.); Viscolam AT100P and Viscolam AT64/P (from Lamberti S.p.A.).

Other materials that may be suitable as polymeric emulsifiers include ethylene oxide/propylene oxide block copolymers, for example those commercialized under the trade name Pluronic® (BASF).

Other suitable polymeric emulsifiers include natural polymer derivatives such as polysaccharides that may be derivatized with hydrophobic moieties. Further examples of suitable emulsifiers that can be used in the topical composition of the present invention are disclosed in "McCutcheon's Detergents and Emulsifiers", North American Edition (2003), Allured Publishing Corporation.

The non-therapeutic cosmetic composition for topical application of the invention can comprise additional cosmetically-functional agents. The term "cosmetically-functional agent", as used herein, means any material, compound or composition which can be applied to skin for cosmetic scope. Non-limiting examples of these agents that may be included in the composition for topical application according to the present invention are the following:

anti-wrinkle agents, such as retinol, hydroxy acids (e.g., alpha-hydroxy acids such as lactic acid and glycolic acid or beta-hydroxy acids such as salicylic acid and salicylic acid derivatives such as the octanoyl derivative) and tocopherols;

anti-oxidants/radical scavengers, such as ascorbic acid and its salts, ascorbyl esters of fatty acids, ascorbic acid derivatives, tocopherol, tocopherol acetate, other esters of tocopherol, gallic acid and its alkyl esters, uric acid and its salts and alkyl esters, sorbic acid and its salts, and the like;

skin coolants, such as menthol, menthyl acetate, and other derivatives of menthol, which give rise to a tactile response in the form of a cooling sensation on the skin;

emollients, such as isopropylmyristate, $C_{12}$-$C_{15}$ alkyl benzoate, silicone materials, mineral oils and vegetable oils which give rise to a tactile response in the form of an increase in skin lubricity;

skin bleaching and lightening agents, such as hydroquinone, kojic acid, arbutin, ascorbic acid and derivatives thereof, extracts (e.g., mulberry extract, placental extract) as well as titanium dioxide and zinc oxide;

sunscreen agents, among which inorganic sunscreen agents (for example metallic oxides such as titanium dioxide, zinc oxide, zirconium oxide, iron oxide, hydroxyapatite and mixtures thereof) and organic sunscreen agents (for example p-aminobenzoic acid, its salts and its derivatives, anthranilates, benzalacetophenone, benzophenones, cinnamic acid derivatives, coumarin derivatives, di hydroxycinnamic acid derivatives, trihydroxy-cinnamic acid derivatives, hydrocarbons, dibenzalacetone, naphtholsulfonates, dihydroxynaphthoic acid and its salts, salicylates, quinine salts, quinoline derivatives, hydroxy- or methoxy-substituted benzophenones, uric and violuric acids, tannic acid and its derivatives, hydroquinone, octocrylene, and mixture thereof;

tanning agents, such as dihydroxyacetone, which is also known as DHA or 1,3-dihydroxy-2-propanone;

skin soothing and/or healing agents, such as panthenoic acid derivatives, for example panthenol, dexpanthenol and ethyl panthenol, aloe vera, retinoids, vitamins and derivatives thereof;

moisturizing agents, that keep the skin moist by either adding moisture or preventing moisture from evaporating from the skin;

topical anesthetics, such as benzocaine, lidocaine, chloroprocaine, dibucaine, etidocaine, tetracaine, procaine, ketamine, pramoxine, phenol, pharmaceutically and cosmetically acceptable salts thereof, and combinations thereof;

perfumes, which give rise to an olfactory response, in the form of a fragrance or deodorant perfumes, which also reduce body malodor;

deodorants other than perfumes, whose function is to reduce the level of or to eliminate micro flora at the skin surface, especially those responsible for the development of body malodor;

beauty aids—such as foundation powders;

shaving actives;

anti-acne agents, such as resorcinol, sulfur, salicylic acid, benzoyl peroxide, erythromycin, zinc, and other similar materials;

chelating agents—such as furildioxime, furilmonoxime, and derivatives thereof;

flavonoids suitable for use on the skin as skin benefit agents, such as unsubstituted flavanones, mono-substituted flavanones, chalcones, flavones, coumarins and mixtures thereof;

steroidal or nonsteroidal anti-inflammatory agents;

antimicrobial agents, such as norfloxacin, tetracycline, ethambutol, erythromycin, phenoxyethanol, phenoxy propanol, methacycline, phenoxyisopropanol, chlorhexidine, chlortetracycline, oxytetracycline, hexamidine isethionate, metronidazole, streptomycin, tetracycline hydrochloride, zinc pyrithione, and combinations thereof;

visual skin enhancers, that mask the appearance of any number of skin imperfections such as age spots, fine lines, wrinkles and blemishes, for example titanium dioxide, zinc oxide and iron oxides and organic particulates that diffuse light when deposited on the skin.

The additional cosmetically-functional agents can be used in concentrations from 0.01 to 30% by weight of the non-therapeutic cosmetic composition for topical application.

The above lists of cosmetically-functional agents are only examples and are not a complete lists of ingredients that can be used. Other agents that can be used in these types of products are well known in the cosmetic industry. In addition to the above cosmetically-functional agents, the composition for topical application according to the present invention can optionally also include other additives, which are conventionally used in the cosmetic industries, such as colorants, preservatives (e.g. imidazolidinyl urea, diazolidinyl urea, phenoxyethanol, methylparaben, ethylparaben, propylparaben, etc.), antifoaming agents, nutritional supplements, activity enhancer, solubilizing agents, functional polymers, thickening agents, stabilizers, suspending agents (such as clays, silica and xanthan), hydrocarbon polymers, medicaments, and mixtures thereof.

Examples of thickening agents that can be used in the composition for topical application of this invention include fatty alcohols; fatty acid esters; fatty acid amides; clays; silicas; anionic, cationic, hydrophobically-modified and amphoteric acrylic copolymers; nonionic, cationic, anionic and amphoteric cellulosic polymers (such as hydroxyethyl cellulose, hydroxypropyl cellulose, carboxymethyl cellulose and cationic hydroxypropyl cellulose); nonionic, anionic, hydrophobically-modified, amphoteric and cationic polysaccharides (such as xanthan, chitosan, carboxymethyl guar, hydroxypropyl guar, cationic hydroxypropyl guar).

The pH is an important factor in the stability of the non-therapeutic cosmetic compositions of the invention. Preferably, the pH range is between 3.5 and 9.0. A wide variety of acids, bases, and buffers can be utilized to adjust and/or maintain the pH of the compositions of the present invention. Examples of materials useful for adjusting and/or maintaining the pH include, without limitation, ammonia, sodium carbonate, sodium hydroxide, triethanolamine, hydrochloric acid, phosphoric acid, sodium hydrogen phosphate, sodium dihydrogen phosphate, citric acid, and the like.

The non-therapeutic cosmetic compositions for topical application onto the skin according to the invention can be formulated as skin lotions, skin creams, body butters, after-shower lotions, after-cleansing lotions, cleansing milk, aftershave products, deodorant products, antiperspirant products, sun care preparations and self-tanning creams. Preferred non-therapeutic cosmetic compositions for topical application are skin creams such as anti-age creams (anti-age day creams, anti-age night creams, eye contour creams, lip contour creams), anti-stretch mark creams (for prevention and reduction) and scar reduction creams; sun care preparations (sunscreens and after-sun) and hand care creams.

For a more detailed disclosing of the invention, reference can be made to the following examples, which are intended as further illustration of the invention and are not to be construed in a limiting sense. All parts and percentages are by weight (wt) unless otherwise stated.

EXAMPLES

Materials

The tuna gonads were obtained from tuna fishes of the species "Thunnus Albacares" caught in the Western and Central Pacific Ocean (Area 71).

Characterization Methods

The % DNA content (by weight) was determined spectrophotometrically at 260 nm on a 50 µg/ml aqueous solution of the non-hydrolyzed nucleic acid material, using the relationship that an Absorbance at 260 nm of 1.0 is equivalent to 50 µg/ml of pure DNA salt.

The % protein content (by weight) of the non-hydrolyzed nucleic acid material was determined using the Lowry assay as described in European Pharmacopeia 5.0, Method 2.5.33, Total Protein.

The % volatile matter (% VM) was determined by weight loss at 105° C. in a fan assisted oven.

The kinematic viscosity (mm$^2$/s) was determined with a Ostwald viscosimeter on a 0.06% by weight water solution of the non-hydrolyzed nucleic acid material.

The UV-Vis absorbance ($A_{428}$) was determined at 428 nm on a 0.003% by weight water solution using a UV-30 SCAN spectrophotometer (Onda) and 1 cm quartz cells. Deionized water was used as blank.

Example 1

100 g of tuna gonads were homogenized for 5 min in a Waring blender with 150 ml of a 0.02 M sodium chloride and 0.002 M sodium citrate aqueous solution. A semi-liquid paste was obtained.

The paste thus produced was transferred in glass reactor equipped with a heater, a rod stirrer and a thermometer and then the following aqueous solutions were sequentially added under stirring:

a) 200 ml of a 0.042 M sodium chloride and 0.002 M sodium citrate solution;
b) 200 ml of a 0.11 wt % sodium lauryl sulfate solution;
c) 200 ml of a 3.85 M sodium chloride solution.

The mass was heated at 60° C. for a period of 4 hours under stirring and at the end it was cooled at a temperature below 10° C.

The sample was then centrifuged at 3800 rpm for 5 min in order to eliminate the heaviest solid components and the liquid supernatant, which consists mainly of nucleic acids, proteins and other smaller materials, was recovered. In order to ease the separation of the protein part, diatomaceous earths, 4% by weight of the recovered supernatant, were dispersed in the liquid under stirring.

A double filtration process was then carried out, first with a filter with larger pore size (5 µm) and then with a smaller pore size (1 µm). The first filter eliminates the majority of the fossil flour and the proteins adsorbed on it, while the second one eliminates all the fine particles and the residues of diatomaceous earths, which were not retained by the first filter.

The nucleic acids were then precipitated from the liquid filtrate, by adding, under stirring, a solution containing cold (5-10° C.) 96% ethanol:3.0 M sodium acetate in a ratio 1:10. The volume of the alcohol mixture was about twice the volume of the liquid filtrate.

After 15 min of stirring, the liquid mass was centrifuged at 3800 rpm for 10 min.

The pellet so obtained was washed, first with a cold 70% v/v ethanol/water mixture and then with room temperature 96% ethanol.

Finally, the non-hydrolyzed nucleic acid material according to the invention was dried at 60° C. and subsequently milled to obtain a ivory white powder.

Example 2

A non-hydrolyzed nucleic acid material according to the present invention was obtained following the same procedure of Example 1, but using a filter with a pore size of 0.8 µm instead of 1.0 µm and washing the pellets obtained from centrifugation first with a cold 70% v/v ethanol/water mixture and then twice with room temperature 96% ethanol.

Example 3 (Comparative)

A comparative sample of hydrolyzed nucleic acid material was prepared following the procedure of Example 1 of KR 2010/0127086.

Table 1 reports the characteristics of the nucleic acid materials of Example 1 and 2 and of comparative Example 3.

The characteristics reported in Table 1 demonstrate the higher overall quality of the non-hydrolyzed nucleic acid materials of the present invention and the superior compatibility with non-therapeutic cosmetic composition for topical application.

TABLE 1

| | Example 1 | Example 2 | Example 3* |
|---|---|---|---|
| Appearance | Fine Powder | Fine Powder | Coarse Powder |
| Colour | White | White | Yellow |
| Odour | Odorless | Slight smell of tuna | Strong smell of tuna |
| % DNA | 83.8 | 87.2 | 29 |
| % Proteins | <1 | <1 | 44.1 |
| % VM | 10.7 | 11.4 | 10.5 |
| Viscosity | 20.1 | 86.2 | — |
| $A_{428}$ | 0.019 | 0.011 | 0.295 |

*Comparative

Fibroblast Proliferation Test

The objective of this test was to investigate the effects of the non-hydrolyzed nucleic acid material of the invention on human skin cells proliferation rate as an valuable aspect of anti-aging activity.

Human skin fibroblast were grown to confluence in culture flasks containing the Dulbecco's modified Eagle's medium (DMEM) containing 10% heated inactivated fetal bovine serum (FBS) and 1% penicillin/streptomycin in a 5% $CO_2$ incubator at 37° C.

96-well flat-bottomed tissue culture plates of good optical quality were inoculated with 10,000 cells/well. Plates were then incubated for 22 hours to permit cell attachment.

Two-fold serial dilutions of the non-hydrolyzed nucleic acid material of Example 1 (final concentrations: 1%-0.5%-0.25%-0.125%-0.0625%-0.031%) were created on each plate, incubated for 24, 48 and 72 hours and assayed. Three replicate plates were prepared for each of the 3 incubation periods.

A column of wells containing cells but no nucleic acid material was used as Control.

Living cell number was measured using the MTT spectrophotometric assay (3-(4,5-dimethylthiazol-2-yl)-2,5-diphenyltetrazolium bromide).

Table 2 report the results as % cell proliferation after 24, 48 and 72 hours in comparison to the Control, which has been considered 100%.

TABLE 2

| | % Nucleic Acid Material | | | | | |
|---|---|---|---|---|---|---|
| | 1.00 | 0.50 | 0.25 | 0.125 | 0.0625 | 0.0312 |
| 24 h | 106 | 108 | 107 | 105 | 103 | 99 |
| 48 h | 104 | 104 | 105 | 103 | 100 | 98 |
| 72 h | 103 | 103 | 102 | 100 | 99 | 99 |

The results of the test demonstrate that the high purity non-hydrolyzed nucleic acid material extracted from tuna has a positive effect on the cell proliferation.

What is claimed is:

1. A non-therapeutic cosmetic method, which comprises the topical application onto the skin of a non-hydrolyzed nucleic acid material extracted from tuna containing more than 75% by weight (wt %) of DNA salts and less than 1.5 wt % of proteins.

2. The non-therapeutic cosmetic method of claim 1, wherein said non-hydrolyzed nucleic acid material contains more than 80 wt % of DNA salts.

3. The non-therapeutic cosmetic method of claim 1, wherein the non-hydrolyzed nucleic acid material extracted from tuna is applied onto the skin as a composition comprising from 0.01 to 5.0 wt % of said non-hydrolyzed nucleic acid material, together with one or more acceptable cosmetic or pharmaceutical carriers or diluents.

4. The non-therapeutic cosmetic method of claim 3, wherein the composition comprises from 0.03 to 3.0 wt % of said non-hydrolyzed nucleic acid material.

5. The non-therapeutic cosmetic method of claim 3, wherein the composition is in the form of an aqueous or hydro-alcoholic system, an emulsion or a gel.

6. The non therapeutic cosmetic method of claim 5, wherein the composition is an emulsion comprising from 0.1 to 15.0 wt % of a emulsifier and from 1.0 to 60 wt % of an oil.

7. The non therapeutic cosmetic method of claim 6, wherein said oil is selected from the group consisting of hydrocarbon oils and waxes, silicone oils, fatty acid derivatives, cholesterol, cholesterol derivatives, diglycerides, triglycerides, natural oils, natural oil derivatives, alkyl or alkenyl esters, lanolin and its derivatives, wax esters, beeswax derivatives and sterols and combinations thereof.

8. The non therapeutic cosmetic method of claim 6, wherein said emulsifier is selected from the group consisting of nonionic, anionic, amphoteric, zwitterionic and cationic emulsifier; natural or synthetic polymeric emulsifiers; and mixtures thereof.

* * * * *